(12) United States Patent
Cohen et al.

(10) Patent No.: US 6,349,442 B1
(45) Date of Patent: *Feb. 26, 2002

(54) BRUSH TIP FOR A MOTORIZED TOOTHBRUSH

(75) Inventors: Howard Cohen, New York, NY (US); Ladislau Biro, Metuchen, NJ (US)

(73) Assignee: Advanced Prosthetic Technologies, Inc., Metuchen, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/338,750

(22) Filed: Jun. 23, 1999

(51) Int. Cl.[7] .......................... A46B 13/02; A61C 17/34
(52) U.S. Cl. ............................................ 15/22.1; 15/28
(58) Field of Search .................... 15/22.1, 28, 21.1, 15/97.1

(56) References Cited

U.S. PATENT DOCUMENTS

| | | | |
|---|---|---|---|
| 1,424,879 A | * | 8/1922 | Carlstedt |
| 1,796,641 A | * | 3/1931 | Zimmerman |
| 1,947,324 A | | 2/1934 | Zerbee |
| 4,158,246 A | * | 6/1979 | Meadows |
| 4,274,173 A | | 6/1981 | Cohen |
| 5,186,627 A | | 2/1993 | Amit et al. |
| 5,416,942 A | | 5/1995 | Baldacci et al. |
| 5,617,601 A | | 4/1997 | McDougall |
| 6,032,313 A | * | 3/2000 | Tsang ........................... 15/28 |

FOREIGN PATENT DOCUMENTS

| | | | | |
|---|---|---|---|---|
| DE | 42 39 251 | | 5/1994 | |
| DE | 295 17 610 | | 4/1997 | |
| DE | 198 03 311 | | 8/1999 | |
| EP | 0 744 139 | | 11/1996 | |
| SE | 0324221 | * | 5/1970 | ................. 15/22.1 |

* cited by examiner

Primary Examiner—Randall E. Chin

(57) ABSTRACT

A brush tip for a motorized toothbrush has a first brush head and a second brush head. The second brush head encircles the first brush head. Means are provided for differently accelerating the first and second brush heads in response to motion produced by the toothbrush motor.

17 Claims, 4 Drawing Sheets

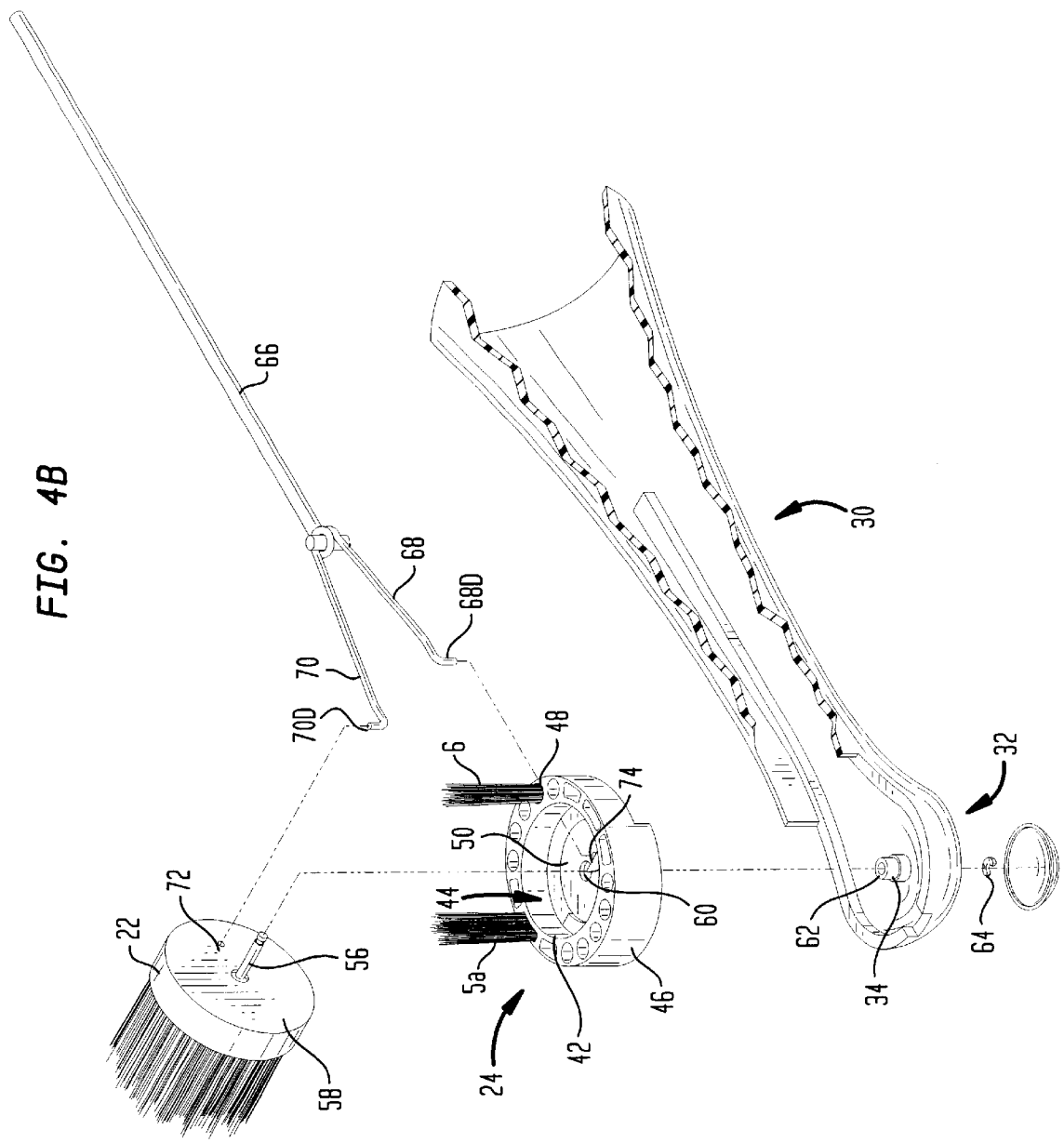

BRUSH TIP FOR A MOTORIZED TOOTHBRUSH

BACKGROUND OF THE INVENTION

The invention relates to toothbrushes, and more particularly relates to powered toothbrushes. In its most immediate sense, the invention relates to a brush tip for a powered toothbrush of the type in which the motor moves a plurality of brush heads.

In a conventional motorized toothbrush of the multi-head type, a disposable brush tip is detachably secured to the handle of the toothbrush. The tip has a plurality of brush heads, which oscillate (as by rotation) under the power of the motor. Each brush head has a plurality of tufts of bristles.

Existing motorized toothbrushes have relatively small "coverage", i.e. they do not clean large surface areas at one time. This is because the brush heads are relatively small. If they are made too large, they will put an excessive load on the motor.

Furthermore, some users operate such toothbrushes improperly. Instead of applying only light pressure, they force the bristles hard against the teeth. Under such conditions, the distal end of each tuft of bristles stays in the same place and the tufts twist themselves tightly in alternate directions. This makes the brushing less effective, because the bristles do not scrub the surfaces of the teeth.

It would be advantageous to provide a multi-head motorized toothbrush that would have greater coverage than conventional toothbrushes.

It would also be advantageous to provide a multi-head motorized toothbrush that would perform better even when the user applies excessive pressure against the tooth surfaces to be cleaned.

In accordance with the invention, a brush tip for a motorized toothbrush has a first brush head and a second brush head. The second brush head encircles the first brush head, and means are provided for differently accelerating the first and second brush heads in response to motion produced by the toothbrush motor.

Because the second brush head encircles the first brush head, the two head together have a relatively large area and, therefore, greater coverage. And, because the two brush heads are accelerated differently, their bristles do not twist themselves together even when pressed hard against the teeth.

In preferred embodiments, the first and second brush heads are accelerated in opposite directions, the first brush head is circular, and the second brush head is elliptical. The elliptical brush head provides greater coverage than a circular brush head and the opposite motions of the heads make it impossible for the bristles attached to the first brush head to twist into the bristles attached to the second brush head.

For toothbrushes of the type wherein the motor produces oscillating rotational motion of a shaft, a gear is mounted at the end of the shaft and is used to rotate the brush heads. For toothbrushes of the type wherein the motor produces reciprocating linear motion of an actuator, two connecting rods are used to convert this linear motion into oscillating rotational motion of the brush heads.

Although the second brush head is advantageously continuous, it need not be so. It may be made up of a plurality of segments thereby having one or more gaps.

BRIEF DESCRIPTION OF THE DRAWINGS

The invention will be better understood with reference to the following illustrative and non-limiting drawings, in which:

FIGS. 4A and 4B are, respectively, a view of a part and an exploded view of a first preferred structure for the FIG. 3 embodiment, this being suitable for use with a motorized toothbrush of the linear motor type;

DETAILED DESCRIPTION OF PREFERRED EMBODIMENTS

Figure 1:
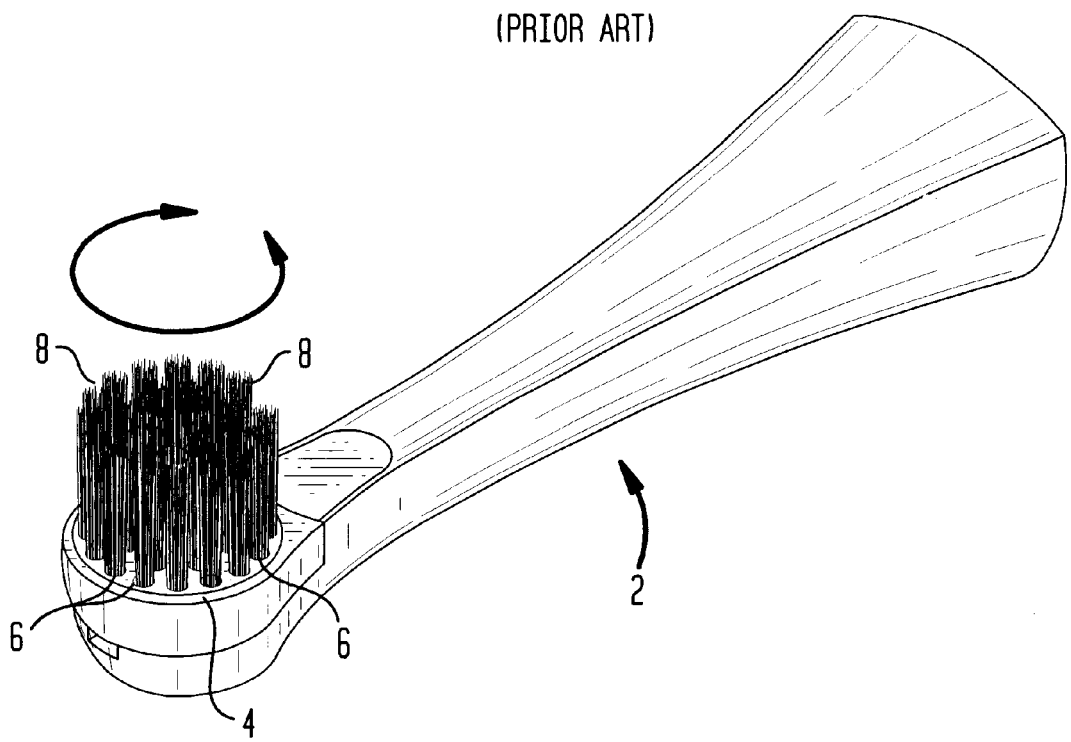
FIG. 1 illustrates a conventional motorized toothbrush with a brush tip of the single head type.

In the following description, the same element is always indicated by the same reference numeral in all the Figures, and corresponding elements are indicated by primed reference numerals. The drawings are not necessarily to scale.

Turning first to FIG. 1, a conventional motorized brush tip generally indicated by reference numeral 2 has a brush head 4 on which tufts 6 of bristles 8 are secured. The brush head 4 is oscillated back and forth by a motor (not shown) while the user (not shown) brushes his or her teeth (not shown).

Figure 2:
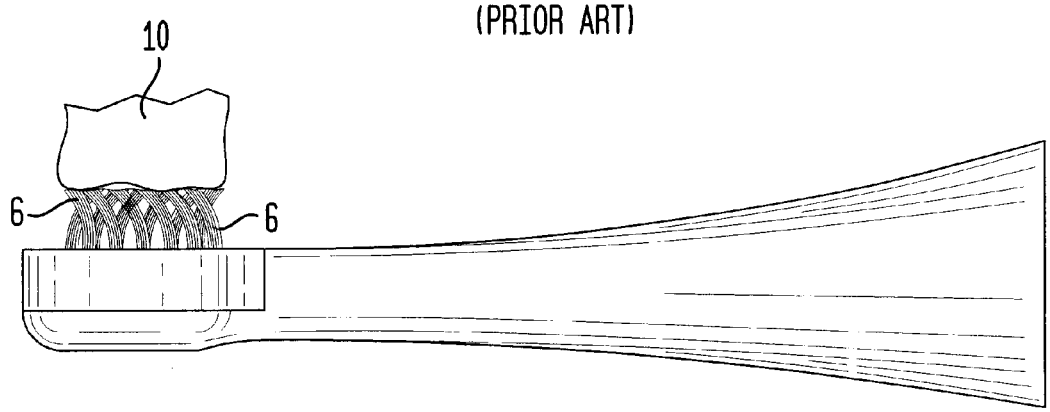
FIG. 2 illustrates how the bristles of the FIG. 1 toothbrush twist together when pressed against a tooth with excessive force.

To use the toothbrush properly, the distal ends of the bristles 8 should not press hard against the surfaces of the teeth. Under such conditions, the bristles 8 scrub the tooth surfaces and remove food particles etc. therefrom. However, as can be seen in FIG. 2, some users apply an excessive pressure to the toothbrush, causing the bristles 8 to press hard against the tooth surface 10. Under such conditions, the bristles 8 do not scrub the tooth surface 10. Instead, the distal ends of the bristles 8 stay fixed in position and the tufts 6 twist tightly against each other. This diminishes the cleaning effectiveness of the toothbrush and also excessively wears the brush tip 2.

In accordance with the preferred embodiment of the invention, a brush tip generally indicated by reference numeral 20 has a first brush head 22 and a second brush head 24. The second brush head 24 encircles the first brush head 22. The first brush head 22 is circular, and the second brush head 24 is elliptical. (Although the second brush head 24 is advantageously elliptical, this is not required and another non-circular shape can be used instead. Furthermore, the second brush head 24 is advantageously continuous, but need not be so. It may be made up of a plurality of segments, and may therefore have one or more gaps.) In further accordance with the preferred embodiment of the invention, means are provided to accelerate the brush heads 22 and 24 differently, i.e. to move in opposite directions. The preferred embodiment therefore provides coverage that is greater than the coverage provided by circular brush heads, since the elliptical second brush head 24 swipes over a wider area. Furthermore, because the first and second brush heads 22 and 24 are accelerated differently, their bristles do not twist together in a knot if the user applies excessive pressure to the toothbrush.

In accordance with the preferred embodiment, the tufts 5a and 6 of bristles 8 on the first and second brush heads 22 and 24 are differently shaped. The tufts 5a are larger and have generally rectangular footprints, while the tufts 6 are smaller and have generally circular footprints. Although the tufts 5a and 6 of bristles 8 are illustrated as being supported by the first and second brush heads 22 and 24 in particular patterns, this is merely exemplary and is not a part of the invention. Other patterns can be used instead. The choice of the patterns in which the tufts 5a and 6 of bristles 8 are arranged is within the capability of a person skilled in the art.

Figure 3:
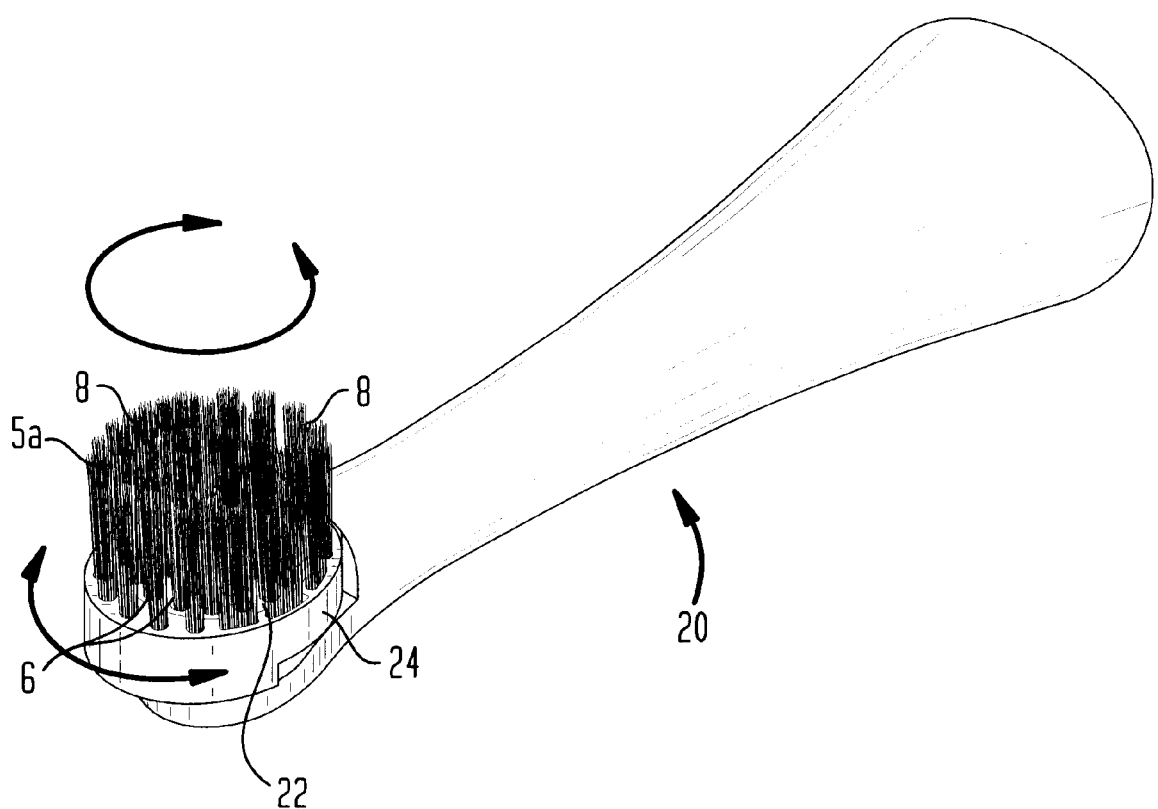
FIG. 3 illustrates a preferred embodiment of the invention.

Mechanisms by which the preferred embodiment may advantageously be operated will now be described in connection with FIGS. 3–5. However, before describing these mechanisms, it is necessary to describe two types of motorized toothbrushes with which the invention is intended to be used.

In one type of motorized toothbrush, the motor causes an actuator (e.g. a plunger) to reciprocate linearly. When the invention is intended for use with this type of toothbrush, this linear reciprocation must be converted to oscillating rotations of the brush heads 22, 24. In another type of motorized toothbrush, the motor causes oscillating rotation of a shaft. When the invention is intended for use with this type of toothbrush, the rotation of the shaft must be transmitted to the brush heads 22, 24. The first type of mechanism will be described first in connection with FIGS. 4–5 and the second type of mechanism will be described next in connection with FIG. 6.

Figure 4A:
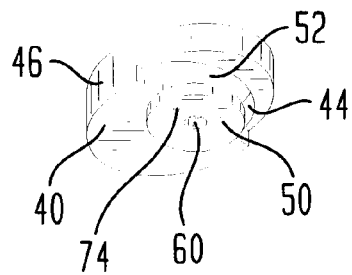

Referring now to FIG. 4, a housing 30 is adapted for attachment to the handle (not shown) of a motorized toothbrush. At the distal end 32 of the housing 30 is located a bearing post 34 upon which the second brush head 24 (described in more detail below) rotates when in use. The first brush head 22 is (as described in more detail below) located within the second brush head 24 in such a manner that the first brush head 22 is free to rotate.

The second bash head 24 has a bottom portion 40, from which a peripheral wall 42 extends upwardly. The interior surface of the wall 42 is cylindrical, creating a cylindrical well 44 in the center of the second brush head 24. (The exterior surface 46 of the wall 42 is elliptical, thereby creating an elliptical annulus 48 at the top of the wall 42 on which tufts 6 of bristles 8 can be supported.)

The surface 50 of the bottom portion 40 forms a bottom surface of the well 44, and a slot 52 is located in the wall 42. The slot 52 is parallel to the bottom surface 50 of the well 44.

The first brush head 22 is cylindrical. Tufts 6 of bristles 8 are supported on its top surface, and an axially extending axle pin 56 projects downwardly from its bottom surface 58. The axle pin 56 extends through a central hole 60 in the second brush head 24 and through a hole 62 in the center of the bearing post 34. A clip 64 at the distal end of the axle pin 56 holds the first brush head 22 within the second brush head 24, and attaches both of them to the housing 30 in such a manner that each brush head 22, 24 can rotate independently of the other. Advantageously but not necessarily, the brush heads 22, 24 are made of Delrin® or other suitable plastic, but this is not a part of the invention and other materials may be used instead.

As stated above, linear motion of a motor-driven actuator 66 must be converted to rotational motion of the first and second brush heads 22 and 24. To do this, first and second connecting rods 68 and 70 are used. The connecting rods 68 and 70 extend through the slot 52 and are formed of a single piece of wire that is generally V-shaped, with the vertex of the V being secured to the actuator 66. (In this preferred embodiment, the wire is bent into a circle at its vertex to facilitate connection with the actuator 66, but this is not required. Advantageously, the wire is of piano wire, or of e.g. nickel-titanium alloy, but other materials may be used instead.) The distal end 70D of the first connecting rod 70 is formed into a hook that engages with a recess 72 in the bottom surface 58 of the first brush head 22, and the distal end 68D of the second connecting rod 68 is formed into a hook that engages with a recess 74 in the bottom surface 50 of the well 44.

Figure 5A:
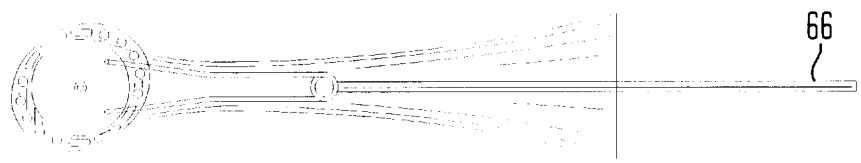
FIGS. 5A, 5B, and 5C illustrate the operation of the structure shown in FIG. 4.
Figure 5B:
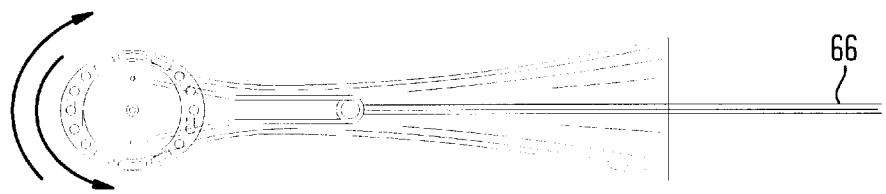
Figure 5C:
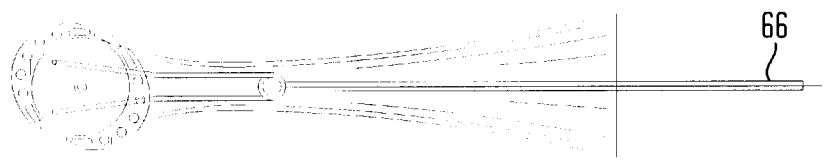

Turning now to FIGS. 5A–5C, when the actuator 66 is at its extreme rearward position (FIG. 5A), the first brush head 22 is rotated to its extreme clockwise position, the second brush head 24 is rotated to its extreme counterclockwise position, and the distal ends 68D and 70D are close together. As the actuator 66 is advanced (FIG. 5B), the connecting rods 68 and 70 move forwardly, their distal ends 68D and 70D move radially outwardly, the first brush head 22 moves counterclockwise, and the second brush head 24 moves clockwise. This continues until the actuator 66 is at its extreme forward position (FIG. 5C), when the first brush head 22 is at its most counterclockwise position, the second brush head 24 is at its most clockwise position, and the distal ends 68D and 70D are close together again. The actuator 66 then moves rearwardly, the above-described motions proceed in reverse, and the linear reciprocation of the actuator 66 is thereby converted to rotational oscillation of the brush heads 22, 24.

It will be understood from the above that the length of the slot 52 is selected to correspond to the arc through which the brushes 22, 24 are rotated during operation. In the preferred embodiment, this arc is 120°, but this is not part of the invention.

Figure 6:
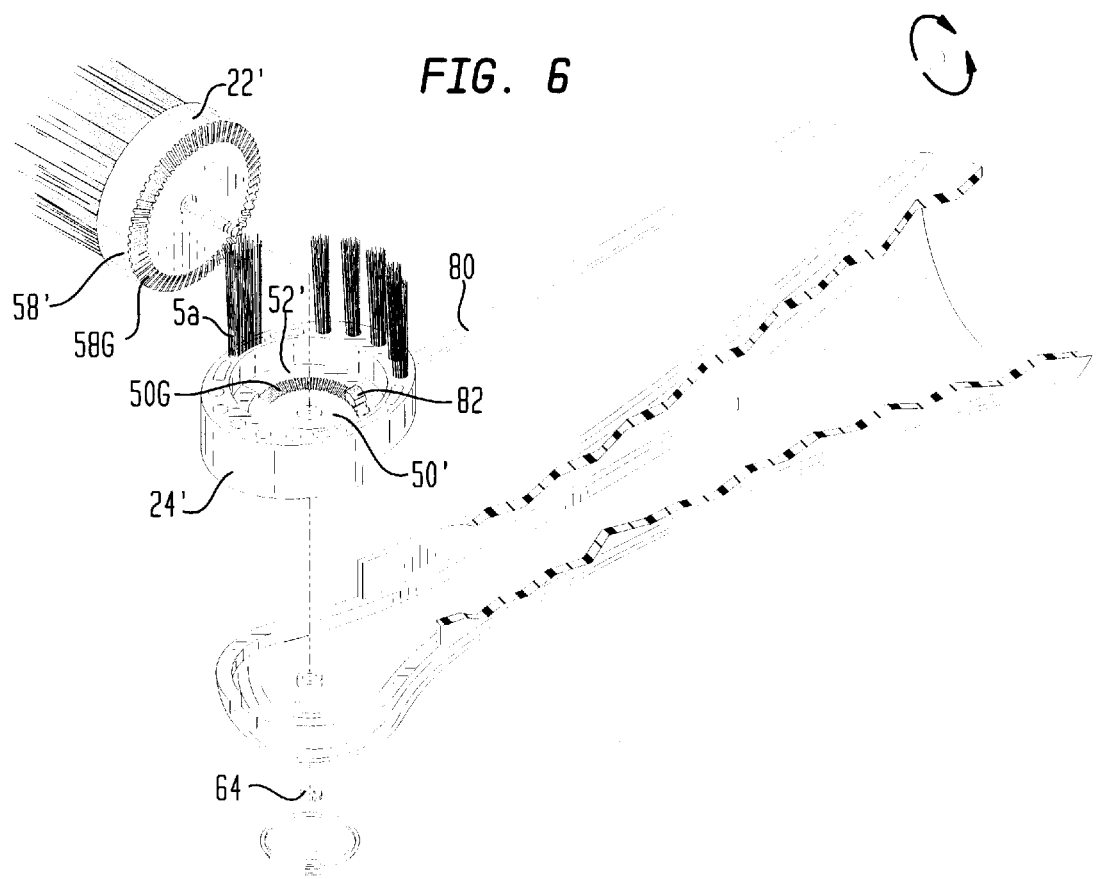
FIG. 6 illustrates the operation of a second preferred structure for the FIG. 3 embodiment, this being suitable for use with a motorized toothbrush of the oscillating motor type.

FIG. 6 shows an alternate structure, for use in instances wherein the motor (not shown) causes a shaft 80 to undergo rotational oscillation. In this structure, the first and second brush heads 22' and 24' have the same general shapes, but there are no connecting rods. Instead, toothed regions 50G and 58G are cut into the bottom surfaces 50' and 58', the shaft 80 extends through the slot 52', and a conical gear 82 at the distal end of the shaft 80 engages the toothed regions 50G and 58G.

It will be understood that the above description may not apply precisely to a production-engineered device. For example, although the surfaces 50, 58 are described as flat, they need not be precisely planar and may even be curved as long as the device as assembled works without excessive play or vibration. Likewise, although the connecting rods 68, 70 are advantageously straight, they may alternatively be slightly bent if this does not interfere with proper operation.

Although at least one preferred embodiment of the invention has been described above, this description is not limiting and is only exemplary. The scope of the invention is defined only by the claims, which follow:

What is claimed is:

1. A brush tip for a motorized toothbrush having a toothbrush motor and a shaft with a conical gear located at a distal end of the shaft, and wherein the toothbrush produces oscillating rotational motion of the shaft and gear, comprising:

a first generally cylindrical brush head having a toothed region on the bottom surface;

a second brush head encircling the first brush head and having a central well with a toothed region on the bottom surface and also having a peripheral wall with a slot therein, the slot extending generally parallel to said bottom surface, the first brush head being located in said well, and the shaft extending into the slot in such a manner that the gear engages with the toothed regions on the first and second brush heads, thereby forming a means for differently accelerating said first and second brush heads in response to motion produced by the toothbrush motor and transmitting said motion to the brush heads in such a manner that the brush heads rotate in opposite senses about a common axis of rotation.

2. The brush tip of claim 1, wherein the first brush head is circular and wherein the second brush head is elliptical.

3. A brush tip for a motorized toothbrush having a toothbrush motor and an actuator, and wherein the toothbrush produces reciprocating linear motion of the actuator, comprising:

a cylindrical first brush head having a flat bottom surface;

a second brush head having a central cylindrical well with a flat bottom surface and a peripheral wall with a slot extending parallel to said bottom surface, the first brush head being located in said well whereby the second brush head encircles the first brush head; and means for differently accelerating said first and second brush heads in response to linear motion produced by the toothbrush motor and transmitting said motion to the brush heads, said differently accelerating means converting said reciprocating linear motion into oscillating rotational motion of the brush heads and comprising first and second connecting rods, each passing through the slot and connecting the actuator with a corresponding one of the brush heads.

4. The brush tip of claim 3, wherein each of the connecting rods has a hook that engages a corresponding recess in the bottom surface of a corresponding one of the brush heads.

5. The brush tip of claim 4, wherein both connecting rods are formed of a single piece of wire.

6. The brush tip of claim 3, wherein the first brush head is circular and wherein the second brush head is elliptical.

7. A brush tip for a motorized toothbrush having a toothbrush motor, comprising:

a first circular brush head;

a second elliptical brush head, the second brush head encircling the first brush head; and means for rotating said first and second brush heads in opposite senses about a common axis of rotation in response to motion produced by the toothbrush motor.

8. A brush tip for a motorized toothbrush having a toothbrush motor, comprising:

a first circular brush head;

a second non-circular brush head, the second brush head encircling the first brush head; and means for differently accelerating said first and second brush heads in response to motion produced by the toothbrush motor.

9. The brush tip of claim 8, wherein said differently accelerating means causes the brush heads to rotate in opposite senses about a common axis of rotation.

10. The brush tip of claim 9, wherein the motorized toothbrush is of a type in which a shaft is driven to undergo oscillating rotational motion, and wherein said differently accelerating means transmits said motion to the first and second brush heads.

11. The brush tip of claim 10, wherein:

the second brush head has a central well with a toothed region on the bottom surface and a peripheral wall with a slot therein, the slot extending generally parallel to said bottom surface;

the first brush head is generally cylindrical with a toothed region on the bottom surface;

the first brush head is located in said well; and the shaft has a conical gear at its distal end and extends into the slot in such a manner that the gear engages with the toothed regions on the first and second brush heads.

12. The brush tip of claim 8, wherein the second brush head is continuous.

13. The brush tip of claim 9, wherein the motorized toothbrush of a type in which an actuator is driven to undergo reciprocating linear motion, and wherein said differently accelerating means converts said reciprocating linear motion into oscillating rotational motion of the brush heads.

14. The brush tip of claim 13, wherein:

the second brush head has a central cylindrical well with a flat bottom surface and a peripheral wall with a slot extending parallel to said bottom surface;

the first brush head is cylindrical and has a flat bottom surface;

the first brush head is located in said well; and further comprising first and second connecting rods, each passing through the slot and connecting the actuator with a corresponding one of the brush heads.

15. The brush tip of claim 14, wherein each of the connecting rods has a hook that engages a corresponding recess in the bottom surface of a corresponding one of the brush heads.

16. The brush tip of claim 15, wherein both connecting rods are formed of a single piece of wire.

17. A brush tip for a motorized toothbrush having a toothbrush motor, comprising:

a first circular brush head;

a second elliptical brush head, the second brush head encircling the first brush head; and means for differently accelerating said first and second brush heads in response to motion produced by the toothbrush motor.

* * * * *